US009416351B2

(12) United States Patent
Janzen et al.

(10) Patent No.: US 9,416,351 B2
(45) Date of Patent: *Aug. 16, 2016

(54) LACTIC BACTERIUM FOR TEXTURIZING FOOD PRODUCTS SELECTED ON BASIS OF PHAGE RESISTANCE

(71) Applicant: CHR. HANSEN A/S, Hoersholm (DK)

(72) Inventors: Thomas Janzen, Broenshoej (DK); Ditte Ellegaard Christiansen, Vanloese (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/719,058

(22) Filed: May 21, 2015

(65) Prior Publication Data

US 2015/0322415 A1 Nov. 12, 2015

Related U.S. Application Data

(60) Continuation of application No. 14/500,134, filed on Sep. 29, 2014, now Pat. No. 9,060,524, which is a division of application No. 13/575,922, filed as application No. PCT/EP2011/051239 on Jan. 28, 2011, now Pat. No. 8,865,238.

(30) Foreign Application Priority Data

| Jan. 28, 2010 | (DK) | ................................ | 2010 00070 |
| Jan. 29, 2010 | (DK) | ................................ | 2010 00081 |
| Jun. 11, 2010 | (DK) | ................................ | 2010 00519 |
| Sep. 1, 2010 | (WO) | ................ | PCT/EP2010/062808 |
| Oct. 1, 2010 | (DK) | ................................ | 2010 00894 |
| Nov. 19, 2010 | (DK) | ................................ | 2010 01051 |

(51) Int. Cl.
| A23C 9/12 | (2006.01) |
| C12N 1/20 | (2006.01) |
| A23C 9/123 | (2006.01) |
| C12N 9/12 | (2006.01) |
| C12R 1/46 | (2006.01) |
| C12N 15/01 | (2006.01) |
| C12N 15/74 | (2006.01) |
| C12Q 1/14 | (2006.01) |

(52) U.S. Cl.
CPC .............. *C12N 9/1205* (2013.01); *A23C 9/123* (2013.01); *A23C 9/1238* (2013.01); *C12N 1/20* (2013.01); *C12N 15/01* (2013.01); *C12N 15/746* (2013.01); *C12Q 1/14* (2013.01); *C12R 1/46* (2013.01); *A23C 2220/202* (2013.01); *A23Y 2220/00* (2013.01); *A23Y 2220/35* (2013.01); *C12Y 207/01006* (2013.01)

(58) Field of Classification Search
CPC .............. C12N 1/20; A23C 9/12; A23C 9/123
USPC .......................................... 435/252.3; 426/43
See application file for complete search history.

(56) References Cited

U.S. PATENT DOCUMENTS

| 7,241,610 | B2 | 7/2007 | Anba et al. |
| 2002/0106754 | A1 | 8/2002 | Tauch et al. |
| 2004/0009490 | A1 | 1/2004 | Glenn et al. |
| 2006/0099197 | A1 | 5/2006 | Farmer |
| 2008/0063752 | A1 | 3/2008 | Perez Martinez et al. |
| 2009/0061046 | A1 | 3/2009 | Tams et al. |
| 2012/0301575 | A1 | 11/2012 | Janzen et al. |
| 2013/0344199 | A1 | 12/2013 | Kibenich et al. |
| 2015/0099273 | A1 | 4/2015 | Janzen et al. |

FOREIGN PATENT DOCUMENTS

| CN | 101175848 | | 5/2008 |
| CN | 101384701 | A | 3/2009 |
| CN | 101505607 | A | 8/2009 |
| WO | WO-2004/085607 | A2 | 10/2004 |
| WO | WO-2004/089098 | A1 | 10/2004 |
| WO | WO-2006/072631 | | 7/2006 |
| WO | WO-2007/025097 | A2 | 3/2007 |
| WO | WO-2007/095958 | A1 | 8/2007 |
| WO | WO-2007/144770 | A2 | 12/2007 |
| WO | WO-2008/040734 | A1 | 4/2008 |
| WO | WO-2008/148561 | A1 | 12/2008 |
| WO | WO-2010/023178 | A1 | 3/2010 |
| WO | WO-2011/000879 | A2 | 1/2011 |
| WO | WO-2011/000883 | A2 | 1/2011 |

OTHER PUBLICATIONS

Amanda Forde et al., "Bacteriophage defence systems in lactic acid bacteria", Antonie van Leeuwenhoek, 1999, pp. 89-113, vol. 76.
Bron et al., "Use of the alr Gene as a Food-Grade Selection Marker in Lactic Acid Bacteria," Applied and Environmental Microbiology, 68(11):5663-5670, Nov. 2002.
Caceres et al., "Overexpression of the D-Alanine Racemase Gene Confers Resistance to D-Cycloserine in *Mycobaterium Smegmatis*," Journal of Bacteriology, 179(16):5046-5055, Aug. 1997.
Daniela M. Guglielmotti et al., "Probiotic potential of *Lactobacillus delbrueckii* strains and their phage resistant mutants," International Diary Journal, 2007, pp. 916-925, vol. 17.
Delcour et al., "The Biosynthesis and Functionality of the Cell-Wall of Lactic Acid Bacteria," Antonie Leeuwenhoek, 76:159-184, (1999).
Ebenezer R. Vedamuthu et al., "Involvement of a Plasmid in Production of Ropiness (Mucoidness) in Milk Cultures by *Streptococcus cremoris* MS", Applied and Environmental Microbiology, Apr. 1986, pp. 677-682, vol. 51, No. 4.
Filip de Vin et al., "Molecular and Biochemical Analysis of the Galactose Phenotype of Dairy *Streptococcus thermophilus* Strains Reveals Four Different Fermentation Profiles", Applied and Environmental Microbiology, Jul. 2005, pp. 3659-3667, vol. 71, No. 7.
Fredrik Levander et al., "Enhanced Exopolysaccharide Production by Metabolic Engineering of *Streptococcus thermophilus*", Applied and Environmental Microbiology, Feb. 2002, pp. 784-790, vol. 68, No. 2.

(Continued)

*Primary Examiner* — Maryam Monshipouri
(74) *Attorney, Agent, or Firm* — Foley & Lardner LLP

(57) ABSTRACT

The present invention relates to a bacterial cell with texturizing property, starter cultures comprising the cell, and dairy products fermented with the starter culture.

9 Claims, 3 Drawing Sheets

(56) References Cited

OTHER PUBLICATIONS

G. Robitaille et al., "Fat-free yogurt made using a galactose-positive exopolysaccharide-producing recombinant strain of *Streptococcus thermophilus*", J. Dairy Science, 2009, pp. 477-482, vol. 92.

G. Robitaille et al., "Galactose Metabolism and Capsule Formation in a Recombinant Strain of *Streptococcus thermophilus* with a Galactose-Fermenting Phenotype", J. Dairy Science, 2007, pp. 4051-4057, vol. 90.

Gabriel Vinderola et al., "Phage-resistant mutants of *Lactobacillus delbrueckii* may have functional properties that differ from those of parent strains", International Journal of Food Microbiology, 2007, pp. 96-102, vol. 116.

Goffin et al., "Lactate Racemization as a Rescue Pathway for Supplying D-Lactate to the Cell Wall Biosynthesis Machinery in *Lactobacillus plantarum*," Journal of Bacteriology, 187(19):6750-6761, Oct. 2005.

Hols et al., "Conversion of *Lactococcus lactis* from homolactic to homoalanine fermentation through metabolic engineering," Nature America, Inc., 17:588-592, Mar. 1999.

Holtje, "Cell Walls, Bacterial," The Desk Encyclopedia of Microbiology, 19:239-250 (2003).

International Search Report for International Application No. PCT/EP2011/068478, mailed Nov. 22, 2011.

International Search Report for International Application No. PCT/EP2011/051239 mailed Mar. 24, 2011.

Katy Vaillancourt et al., "Characterization of a Galactokinase-Positive Recombination Strain of *Streptococcus thermophilus*", Applied and Environmental Microbiology, Aug. 2004, pp. 4596-4603, vol. 70, No. 8.

Li et al., "Non-antibiotic Resistance Selection Marker Systems for Lactic Acid Bacteria," Chinese Journal of Biochemistry and Molecular Biology, 23 (1) 2007, 7 pages.

M. Svensson et al. "Altered nucleotide sugar metabolism in *Streptococcus thermophilus* interferes with nitrogen metabolism", International Journal of Food Microbiology, 2007, pp. 195-200, vol. 113.

Mustafa Akcelik et al., "Characterisation of an Exopolysaccharide Preventing Phage Adsorption in *Lactococcus lactic* subsp. *cremoris* MA39", Turk. J. Vet. Anim. Sci., 2002, vol. 26, pp. 1151-1156.

Notice of Allowance dated Jun. 18, 2014 issued in connection with U.S. Appl. No. 13/575,922.

Notice of Allowance dated Feb. 18, 2015 issued in connection with U.S. Appl. No. 14/500,134.

Office Action dated Oct. 1, 2014 issued in U.S. Appl. No. 13/880,620.

Office Action dated Nov. 20, 2013 issued in U.S. Appl. No. 13/575,922.

Park et al., "D-Alanyl-D-Lactate and D-Alanyl-D-Alanine Synthesis by D-Alanyl-D-Alanine Ligase from Vancomycin-resistant *Leuconostoc mesenteroides*," The Journal of Biological Chemistry, 272(14):9210-9214, Apr. 1997.

Rivals et al., "Cryotolerance of *Lactobacillus delbrueckii* subsp. *bulgaricus* CFL1 is modified by acquisition of antibiotic resistance," Cryobiology, 55:19-26, Apr. 2007.

Sacha Lucchini et al., "Broad-Range Bacteriophage Resistance in *Streptococcus thermophilus* by insertional Mutagenesis", Virology, 2000, pp. 267-277, vol. 275.

Second Office Action dated Apr. 14, 2014 issued in connection with Chinese Application No. 201180007721.X, with English translation.

Tytgat et al., "DD-Ligases as a Potential Target for Antibiotics: Past, Present and Future," Current Medicinal Chemistry, 16:2566-2580 (2009).

Written Opinion for International Application No. PCT/EP2011/068478 mailed Feb. 20, 2013.

Bhaskaracharya et al., "Texture characteristics and microstructure of skim milk mozzarella cheeses made using exopolysaccharide or non-exopolysaccharide producing starter cultures", *Australian Journal of Diary Technology*, vol. 55(3): 132-138, Oct. 2000.

Office Action dated May 1, 2015 issued in U.S. Appl. No. 13/880,620.

Andre et al., "Imaging the nanoscale organization of peptidoglycan in living Lactococcus lactis cells", Nature Communications, vol. 1: 27 (Jun. 2010).

De Vuyst et al.; "Heteropolysaccharides from lactic acid bacteria", FEMS Microbiology Reviews 23: 153-77 (Apr. 1999).

USPTO Final Office Action issued in U.S. Appl. No. 13/880,620 dated Nov. 12, 2015; 17 pages.

LACTIC BACTERIUM FOR TEXTURIZING FOOD PRODUCTS SELECTED ON BASIS OF PHAGE RESISTANCE

FIELD OF INVENTION

The present invention relates to a bacterial cell which has improved phage resistance, starter cultures comprising the cell, and dairy products fermented with the starter culture.

BACKGROUND OF INVENTION

The food industry uses numerous bacteria, in particular lactic bacteria, in order to improve the taste and the texture of foods but also in order to extend the shelf life of these foods. In the case of the dairy industry, lactic bacteria are used intensively in order to bring about the acidification of milk (by fermentation) but also in order to texturize the product into which they are incorporated.

Among the lactic bacteria used in the food industry, there can be mentioned the genera *Streptococcus, Lactococcus, Lactobacillus, Leuconostoc, Pediococcus* and *Bifidobacterium*. The lactic bacteria of the species *Streptococcus thermophilus* are used extensively alone or in combination with other bacteria for the production of food products, in particular fermented products. They are used in particular in the formulation of the ferments used for the production of fermented milks, for example yogurts. Certain of them play a dominant role in the development of the texture of the fermented product. This characteristic is closely linked to the production of polysaccharides. Among the strains of *Streptococcus thermophilus* it is possible to distinguish texturizing and non-texturizing strains.

WO2007095958A1 discloses *Streptococcus thermophilus* strains with texturizing properties. In FIG. 1 it can be seen that the most texturizing strain CHCC8833 (DSM17876) has a shear stress value of around 59 Pa.

In order to meet the requirements of the industry, it has become necessary to provide novel texturizing strains of lactic bacteria, in particular of *Streptococcus thermophilus*, for texturizing food products. Especially there is a need for a novel texturizing strain of *Streptococcus thermophilus* which can be used together with a strain of a *Lactobacillus* species. Another need of the industry is that the strain is resistant to bacteriophages normally found in the food industry.

SUMMARY OF INVENTION

The present inventors have provided a novel group of lactic acid bacteria of the species *Streptococcus thermophilus* and *Lactobacillus bulgaricus*, which surprisingly is more resistant to phage attack than the (mother) strain from which it is obtained. Further, it has surprisingly turned out that this group of bacteria generates higher shear stress and/or gel stiffness than the mother strain when the bacteria are used for fermenting milk.

It is surprising that a phage resistant mutant strain generates more texture, e.g. higher shear stress and/or gel stiffness, (when the strain is used to ferment milk) than the mother strain, and it is especially surprising that a phage resistant mutant strain of a strain which (also) contains a mutation in the galK gene (relative to the wildtype strain) generates more texture (when the strain is used to ferment milk) than the mother strain.

In accordance with the above surprising findings, the present invention relates to a method for manufacturing a texturizing lactic acid bacterium strain by screening for phage resistant mutants of a mother strain, e.g. a method for manufacturing a texturizing lactic acid bacterium (e.g. a bacterium which, besides being e.g. phage resistant, substantial phage resistant, and/or possesses increased phage resistance compared to the mother stain, is more texturizing than the mother strain), comprising the steps:
a) Providing a lactic acid bacterial strain (the mother strain); and
b) Isolating a mutant strain of the mother strain, which mutant strain is resistant against more phages (e.g. more types of phages or more strains of phages) than the mother strain.

Further, the present invention relates to texturizing lactic acid bacteria strains, such as *S. thermophilus* strains or *Lactobacillus bulgaricus* stains, which are modified to be resistant to more phages than the mother strain, in particular against one of the phages CHPC658, CHPC1057, CHPC1089 and CHPC1152.

DETAILED DISCLOSURE

In a first aspect, the present invention relates to a method for manufacturing a lactic acid bacterium (which is e.g. phage resistant, substantial phage resistant, and/or possesses increased phage resistance compared to the mother stain, or which generates higher shear stress and/or gel stiffness than the mother strain when the bacteria are used for fermenting milk), comprising the steps:
a) Providing a lactic acid bacterial strain (the mother strain); and
b) Isolating a mutant strain of the mother strain, which mutant strain is resistant against more phages (e.g. more types of phages or more strains of phages) than the mother strain, and/or which mutant is resistant against a phage which the mother strain is not resistant to (under that same conditions).

In an interesting aspect, the present invention relates to a method for manufacturing a lactic acid bacterium (which is e.g. phage resistant, substantial phage resistant, and/or possesses increased phage resistance compared to the mother stain and/or which generates higher shear stress and/or gel stiffness than the mother strain when the bacteria are used for fermenting milk), comprising the steps:
a) Providing a lactic acid bacterial strain (the mother strain); and
a1) Exposing the lactic bacterial strain to a bacteriophage, e.g. a bacteriophage which is able to lyse the mother strain, such as a phage selected from the group consisting of CHPC658, CHPC1057, CHPC1089 and CHPC1152, and;
b) Isolating a mutant strain of the mother strain, which mutant strain is resistant against the phage (or which strain is not lysed by the phage).

Also, the present invention relates to a method, comprising the steps:
a) Providing a lactic acid bacterial strain (the mother strain);
a1) Exposing the lactic bacterial strain to a bacteriophage, e.g. a bacteriophage which is able to lyse the mother strain, such as a phage selected from the group consisting of CHPC658, CHPC1057, CHPC1089 and CHPC1152;
a2) Incubating the exposed bacterial cells in a growth medium; and
b) isolating a mutant strain of the mother strain, which mutant strain is not lysed by the bacteriophage
The methods of the invention may comprise the step
c) mutating (e.g. by chemical treatment or radiation treatment, or by means of genetic engineering techniques) the mother strain, e.g. before, during or after step a1).
Also, any method of the invention may comprise the step d) introducing a mutation in the galK gene or the galK regulatory sequence (e.g. promoter) of the strain (e.g. by chemical treatment or radiation treatment, or by means of genetic engineering techniques), e.g. before, during or after step c), or before, during or after step a1).

In an interesting embodiment, a method of the invention comprises the steps:

Providing a lactic acid bacterial strain (the mother strain);

mutating (e.g. by chemical treatment or radiation treatment, or by means of genetic engineering techniques) the mother strain;

Exposing the resulting lactic bacterial strain to a bacteriophage, e.g. a bacteriophage which is able to lyse the mother strain, such as a phage selected from the group consisting of CHPC658, CHPC1057, CHPC1089 and CHPC1152;

Incubating the exposed bacterial cells in a growth medium; and isolating a mutant strain of the mother strain, which mutant strain is not lysed by the bacteriophage;

The method of the invention may lead to that a mutation is introduced in the promoter region of the galK gene, such as in the −10 region (the Pribnow box) or in the region between the Pribnow box and the ribosome binding site.

Also, the method of the invention may lead to a mutation resulting in increased galactose fermenting activity compared to the mother strain.

The mutation may result in the replacement of one or more nucleotides in the region between the Pribnow box and the ribosome binding site of the galK gene, such as replacement of C in the sequence TTCAGT downstream from the wildtype Pribnow box with a nucleotide selected from the group consisting of A, T and G.

In an other embodiment, the mutation may result in:

the replacement of one or more nucleotides in the region between the Pribnow box and the ribosome binding site of the galK gene, such as replacement of C in the sequence TTCAGT (SEQ ID NO:6) downstream from the wildtype Pribnow box with a nucleotide selected from the group consisting of A, T and G; and/or the replacement of one or both of C and G in the wildtype −10 region (TACGAT, SEQ ID NO:7) with a nucleotide independently selected from the group consisting of A and T; and/or the replacement of C the wildtype −10 region (TACGAT, SEQ ID NO:7) with a nucleotide independently selected from the group consisting of A and T; and/or the replacement of C the wildtype −10 region (TACGAT, SEQ ID NO:7) with T; and/or a −10 region which has the nucleotide sequence TATGAT (SEQ ID NO:8), TATTAT (SEQ ID NO:9) or TACTAT (SEQ ID NO:10).

It should be understood that the mother strain used in a method of the invention may be a gal+ strain, preferable a strain which is able to reduce pH by a value of at least 1.0 after 16 hours incubation at 37 degrees C. in M17 with 2% galactose (galactose added as sole carbohydrate), inoculated in an amount of at least 10E4 cells pr ml of medium. Examples on such a strain is a strain wherein:

one or more nucleotides in the region between the Pribnow box and the ribosome binding site of the galK gene has been replaced, such as replacement of C in the sequence TTCAGT (SEQ ID NO:6) downstream from the wildtype Pribnow box with a nucleotide selected from the group consisting of A, T and G; and/or one or both of C and G in the wildtype −10 region (TACGAT, SEQ ID NO:7) has been replaced with a nucleotide independently selected from the group consisting of A and T; and/or C in the wildtype −10 region (TACGAT, SEQ ID NO:7) has been replaced with a nucleotide independently selected from the group consisting of A and T; and/or C in the wildtype −10 region (TACGAT, SEQ ID NO:7) has been replaced with T; and/or the −10 region has the nucleotide sequence TATGAT (SEQ ID NO:8), TATTAT (SEQ ID NO:9) or TACTAT (SEQ ID NO:10). Novel gal+ strains is a part of the present invention.

The method of the invention may comprise one or more further step(s) selected from the group consisting of:

c1) screening for a mutant strain having phage resistance, such as increased phage resistance compared to the mother stain; and c2) screening for a mutant strain having Gal+ phenotype, such as increased galactose degrading activity compared to the mother stain.

An embodiment of the method of the present invention relates to a method for manufacturing a lactic acid bacterium, comprising the steps:

Providing a lactic acid bacterial strain (the mother strain);

optionally mutating the mother strain;

Exposing the optionally mutated mother strain to a bacteriophage, e.g. a bacteriophage which is able to lyse the mother strain, such as a phage selected from the group consisting of CHPC658, CHPC1057, CHPC1089 and CHPC1152;

optionally incubating the exposed bacterial cells with a growth medium; and screening for a mutant strain having phage resistance, such as increased phage resistance compared to the mother strain; and/or screening for a mutant strain having Gal+ phenotype, such as increased galactose degrading activity compared to the mother stain.

The mutant strain obtained by a method of the invention may be a spontaneous mutant, a mutant obtained by mutagenesis of the mother strain by means of e.g. chemical treatment or radiation treatment, or a mutant obtained by means of genetic engineering techniques. An interesting mutant of the invention is a mutant of CHCC6008, esp. a mutant which is gal+ and resistant against CHCP1152.

In an embodiment of the method of the invention, the mutant strain is phage resistant, substantial phage resistant, and/or possesses increased phage resistance compared to the mother stain, and wherein the phage is selected from the group consisting of: a bacteriophage which is able to lyse the mother strain, CHPC658, CHPC1057, CHPC1089 and CHPC1152.

It is presently preferred that the bacterium (the mother strain) is selected from a species selected from the group consisting of *Lactococcus* spp., *Streptococcus* spp. (e.g. *Streptococcus thermophilus*), *Lactobacillus* spp., *Leuconostoc* spp., *Pseudoleuconostoc* spp., *Pediococcus* spp., *Brevibacterium* spp., *Enterococcus* spp., *Propionibacterium* spp, and *Bifidobacterium* spp.

In an interesting embodiment of a method of the invention, the bacterium (the mother strain) is selected from a strain which has one or more features selected from the group consisting of: ability to texturize milk, ability to produce a polysaccharide, such as an exopolysaccharide or a capsular polysaccharide, ability to create viscosity when incubated in milk, and ability to increase shear stress when incubated in milk.

In another aspect, the present invention relates to a lactic acid bacterium or strain which is obtainable by a method of the invention.

In a further aspect, the present invention relates to a lactic acid bacterium or strain, such as a bacterium or strain obtainable by a method of the invention, which generates a viscosity in fermented milk greater than about 70 Pa (pascal) (such as greater than 73 Pa, greater than 77 Pa or greater than 79 or greater than 80 Pa), measured as shear stress after 12 hours of growth at 37 degrees C., e.g. inoculated in an amount of at least 10E4 cells pr ml of milk. It is believed that it is possible to obtain strains which generates a viscosity in fermented milk up to 100 Pa, up to 120 Pa, up to 150 Pa, or even up to 200 Pa. Examples of ranges for viscosity obtainable are: 70 to 200 Pa, 75 to 150 Pa, 78 to 120 Pa, 79 to 100 Pa, and 80 to 90 Pa. Especially, the present invention relates to a strain of *S. thermophilus*, which is able to generate a viscosity of 79 to 100 Pa in fermented milk.

Examples of a strain of the invention is a bacterial strain belonging to the species *Streptococcus thermophilus*, selected from the group consisting of: CHCC11342 (DSM 22932), CHCC11977 (DSM22935), CHCC12339 (DSM24090), and CHCC13140 (DSM 24023), and mutants and variants of any of these. In addition, the invention relates to all novel strains mentioned herein, as well as their mutants and variants. Specifically, the present invention relates to the strain CHCC11977, and a mutant thereof.

In a further aspect the present invention relates to a lactic acid bacterium or strain of the invention, which generates a shear stress in fermented milk greater than about 70 Pa (such as greater than 73 Pa, greater than 77 Pa or greater than 80 Pa), measured after 12 hours of growth at 37 degrees C., e.g. inoculated in an amount of at least 10E4 cells pr ml of milk. The bacterium or strain may belong to the species *Streptococcus thermophilus* or *Lactobacillus delbrueckii* subsp. *bulgaricus*.

The present invention also relates to a bacterial strain belonging to the species *Lb delbrueckii* sbsp. *bulgaricus*, such as a strain selected from the group consisting of CHCC12813 (DSM24074) and CHCC12841, and mutants and variants thereof. Interesting strains are those which generates a shear stress in fermented milk greater than about 60 Pa (such as greater than 65 Pa, greater than 69 Pa or greater than 72 Pa), measured after 12 hours of growth at 37 degrees C., e.g. inoculated in an amount of at least 10E4 cells pr ml of milk. Especially interesting are those generating a shear stress in fermented milk in the range from 60 to 100 Pa (such as from 65 to 90 Pa, from 69 to 85 Pa or from 72 to 80 Pa), measured after 12 hours of growth at 37 degrees C., e.g. inoculated in an amount of at least 10E4 cells pr ml of milk.

In a still further aspect the present invention relates to a lactic acid bacterium or strain or mutant or variant of the invention, which generates a gel stiffness in fermented milk greater than about 110 Pa (such as greater than 115, greater than 120 or greater than 125 Pa), measured after 12 hours of growth at 37 degrees C., e.g. inoculated in an amount of at least 10E4 cells pr ml of milk. It is presently preferred that the gel stiffness is within the range 110 to 200 Pa, or more preferred within the range 120 to 190 Pa or 125 to 180 Pa. The bacterium or strain may belong to the species *Streptococcus thermophilus* or *Lactobacillus delbrueckii* subsp. *bulgaricus*. Especially, the present invention relates to a strain of *S. thermophilus*, which is able to generate a gel stiffness of 125 to 175 Pa in fermented milk.

In an interesting embodiment, the present invention relates to a lactic acid bacterium or strain, which belongs to the species *Lb. delbrueckii* sbsp. *bulgaricus*. Interesting examples on this embodiment are a bacterium or strain, which generates a viscosity in fermented milk greater than about 60 Pa (such as greater than 65 Pa, greater than 69 Pa or greater than 72 Pa), measured as shear stress after 12 hours of growth at 37 degrees C., e.g. inoculated in an amount of at least 10E4 cells pr ml of milk, and/or a bacterium or strain, which generates a viscosity in fermented milk in the range from 60 to 100 Pa (such as from 65 to 90 Pa, from 69 to 85 Pa or from 72 to 80 Pa), measured as shear stress after 12 hours of growth at 37 degrees C., e.g. inoculated in an amount of at least 10E4 cells pr ml of milk.

In an other aspect, the present invention relates to a composition comprising lactic acid bacteria or a strain of the invention, such as bacteria belonging to the strain CHCC11977 or a mutant thereof. It is preferred that such composition comprises at least 10exp10 CFU (cell forming units) of said bacteria.

In an embodiment, the composition may comprise, either as a mixture or as a kit-of-parts, a strain belonging to a *Lactobacillus* species, such as a *Lactobacillus delbrueckii* subsp. *bulgaricus* (synonym: *Lactobacillus bulgaricus*), a *L. johnsonii*, or a *L. fermentum* strain; and a strain of a lactic acid bacterium of the invention, such as a strain belonging to the species *Streptococcus thermophilus*, e.g. a strain selected from the group consisting of CHCC11342 (DSM 22932), CHCC11977 (DSM22935), CHCC12339, and CHCC13140 (DSM 24023), and mutants and variants of any of these, such as a composition wherein the strain belonging to a *Lactobacillus* species is a strain belonging to a polysaccharide (such as a heteropolysaccharide, homopolysaccharide) and/or fructosyl transferase enzyme producing *Lactobacillus* species.

The composition of the invention may comprise at least 10exp10 CFU (cell forming units) of a strain belonging to a *Lactobacillus* species; and/or at least 10exp10 CFU of a strain belonging to the species *Streptococcus thermophilus*.

In an interesting embodiment, the composition of the invention comprises at least 10exp10 CFU (cell forming units) of a strain belonging to a polysaccharide (such as homopolysaccharide) and/or fructosyl transferase enzyme producing *Lactobacillus* species; and at least 10exp10 CFU of a strain belonging to the species *Streptococcus thermophilus*.

The composition may be usable as a starter culture, and may be in frozen, freeze-dried or liquid form.

In a further aspect, the present invention relates to a method for producing a fermented milk product, comprising fermenting a milk substrate (such as cow's milk) with a lactic acid bacterium of the invention, a strain of the invention, or a composition of the invention.

This method may further comprise fermenting the milk substrate with a strain belonging to a *Lactobacillus* species, such as a strain of *L. bulgaricus* or *L. fermentum*, e.g. a strain selected from the group consisting of CHCC10019, CHCC10935, or CHCC3984, and mutants and variants of any of these strains. E.g., the milk substrate is fermented with a composition, strain or bacterium of the invention, such as a strain belonging to the species *Streptococcus thermophilus* before, during, or after the fermentation with a strain belonging to a *Lactobacillus* species, or, the milk substrate is fermented with a strain or bacterium belonging to the species *Streptococcus thermophilus* during the fermentation with a strain belonging to a polysaccharide producing *Lactobacillus* species.

The method of the invention for producing a fermented milk product may comprise adding an enzyme to the milk substrate before, during and/or after the fermenting, such as an enzyme selected from the group consisting of: an enzyme able to crosslink proteins, transglutaminase, an aspartic protease, chymosin, and rennet.

In yet another aspect, the present invention relates to a dairy product, such as a fermented milk product (e.g. yoghurt or buttermilk) or a cheese (e.g. fresh cheese or pasta filata), obtainable by the above method of invention. The fermented milk product may e.g. be a stirred-type product, a drinkable product, or a set-type product. The dairy product of the invention may optionally comprise an ingredient selected from the group consisting of: a fruit concentrate, a syrup, a probiotic bacterial culture, a coloring agent, a thickening agent, a flavoring agent, and a preserving agent.

Thus, the present invention relates to a fermented milk product obtainable by the method of the invention, which optionally comprises an ingredient selected from the group consisting of: a fruit concentrate, a syrup, a probiotic bacterial culture, a coloring agent, a thickening agent, a flavoring agent, and a preserving agent; and/or which optionally is in the form of a stirred type product, a set type product, or a drinkable product.

Also the invention relates to a dairy product, which is made by fermenting a milk substrate (such as cow's milk) with a lactic acid bacterium of the invention (e.g. a strain belonging to the species *Streptococcus thermophilus*, such as DSM 22884) and a lactic acid bacterium a species selected from *Lactobacillus bulgaricus* and *Lactobacillus fermentum* (such as CHCC10019 (DSM19252), CHCC3984 (DSM19251) and CHCC2008 (DSM22584)).

In an interesting embodiment, a dairy product of the invention has a viscosity/texture of more than 100 Pa (such as more than 102 or more than 104 Pa), measured as shear stress, e.g. after 12 hours growth at 37 degrees C. in milk. In a presently preferred embodiment, the viscosity of more than 100 Pa is obtained by growth of the bacterial cells alone, but higher viscosity values can be obtained by addition of chemical compounds, such as starch, gelatine, a carrageenan, etc.

In an other embodiment, the dairy product of the invention has a viscosity/texture in the range of 100 to 200 Pa, such as in the range of 100 to 150 Pa, or in the range of 105 to 125 Pa, measured as shear stress.

In a further embodiment, the dairy product of the invention is a drinkable product, e.g. drinking yoghurt.

The invention also relates to novel bacteriophages usable in a method of the invention, such as a bacteriophage selected from the group consisting of CHPC658 (DSM 23961), CHPC1057, CHPC1089 and CHPC1152 (DSM 23994), and mutant and variants thereof, such as mutants and variants which are able to lyse strains mentioned herein, e.g. the strain CHCC6008.

Further, the invention relates to novel bacterial strains, useable as mother strains in a method of the invention, such as strains selected from the group consisting of CHCC11342 (DSM22932), CHCC10019 (DSM19252), CHCC11379 (DSM 22884), CHCC11976 (DSM 22934), and mutants thereof.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

The term "milk" is to be understood as the lacteal secretion obtained by milking any mammal, such as cows, sheep, goats, buffaloes or camels. In a preferred embodiment, the milk is cow's milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "stirred type product" specifically refers to a fermented milk product which sustains a mechanical treatment after fermentation, resulting in a destructuration and liquefaction of the coagulum formed under the fermentation stage. The mechanical treatment is typically but not exclusively obtained by stirring, pumping, filtrating or homogenizing the gel, or by mixing it with other ingredients. Stirred type products typically but not exclusively have a milk solid non-fat content of 9 to 15%.

The term "set-type product" includes a product based on milk which has been inoculated with a starter culture, e.g. a starter culture, and packaged next to the inoculating step and then fermented in the package.

The term "drinkable product" includes beverages such as "drinking yoghurt" and similar. The term "drinking yoghurt" typically covers a milk product produced by fermentation by the combination of *Lactobacillus* species and *Streptococcus thermophiles*. Drinking yoghurt typically has a milk solid non-fat content of 8% or more. Furthermore, the live culture count for drinking yoghurt drinks is typically at least 10E6 cell forming units (CFU) pr ml.

"Drinkable product" according to the present invention include any drinkable product based on acidified milk substrates, thus including fermented milk drinks and liquid yoghurt drinks. In the methods of the present invention, acidification is performed as a fermentation with a microorganism, optionally an acid is added, such as an organic acid (e.g. lactic acid, lactobionic acid or GDL).

Drinkable products according to the invention are drinkable in the sense that they are in liquid form and consumed as beverages, i.e. they are suitable for drinking instead of being eaten with a spoon. "In liquid form" means that the products are in the fluid state of matter thus exhibiting a characteristic readiness to flow. Thus, the shape of a liquid is usually determined by the container it fills, in contrary to e.g. a gel-like substance, which is soft, but not free flowing, such as e.g. yoghurt or pudding. Drinkable products according to the invention may have a viscosity allowing the consumer to drink the products using a straw if desired.

An drinkable product according to the present invention may have a pH of less than 4.6, preferably less than 4.4, more preferably less than 4.2 and even more preferably about pH 4 or less. In one aspect, the drinkable product has a pH of less than 3.8, such as less than 3.6.

An drinkable product according to the invention may have a fat content of 0 to 2%, preferably below 1.5%, below 1% or below 0.5%, more preferably of about 0.1% or less. The drinkable product may have a milk solid non-fat content of less than 20%, preferably less than 8.5%, less than 8%, less than 7.5%, less than 7%, less than 6.5% or less than 6%, and more preferably of about 5%.

An drinkable product according to the invention may have a protein content of between 0.5 and 4%. In one preferred aspect, the drinkable product has a protein content of below 1%. In another preferred aspect, the drinkable product has a protein content of between 2% and 3%.

An drinkable product according to the invention may have a shelf life of more than 7 days, preferably more than 14 days, more preferably more than 28 days, such as more than 3 months.

An drinkable product according to the present invention may have an improved sedimentation stability. The stability may be determined after having stored the drinkable product for an appropriate number of days by measuring the height of the whey collecting on the surface because of syneresis. It may also be determined after accelerated syneresis, such as by centrifugation.

For a drinkable product, e.g. drinking yoghurt, a high shear treatment (e.g. homogenization) after fermentation is normally needed to break down the protein network in order to obtain smooth, homogeneous and drinkable products. The breakdown of the network implies that drinking yoghurts have a reduced sedimentation stability, resulting in sedimentation of protein to the bottom during shelf life. High fat revels and high protein content increase sedimentation stability, while low fat products (0-0.5% fat) with low protein levels (1-2.5%) normally needs addition of a stabilizer to avoid protein sedimentation.

As used herein, the term "bacteriophage" has its conventional meaning as understood in the art ie. a virus that selectively infects one or more bacteria. Many bacteriophages are specific to a particular genus or species or strain of bacteria. The term "bacteriophage" is synonymous with the term "phage". Bacteriophages may include, but are not limited to, bacteriophages that belong to any of the following virus families: Corticoviridae, Cystoviridae, Inoviridae, Leviviridae, Microviridae, Myoviridae, Podoviridae, Siphoviridae, or Tectiviridae. The bacteriophage may be a lytic bacteriophage or a lysogenic bacteriophage. A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells. A lysogenic bacteriophage is one capable of entering the lysogenic pathway, in which the bacteriophage becomes a dormant, passive part of the cell's genome through prior to completion of its lytic cycle.

In one embodiment, the lactic acid bacterium according to the present invention is resistant to one or more bacteriophage or one or more sets of bacteriophages, in another embodiment, the lactic acid bacterium according to the present invention is resistant to the same bacteriophage that a strain deposited according to the present invention is resistant to. In the present context, the term "phage robust" is used interchangeable with the term "phage resistant".

In the present context, the term "mutant" should be understood as a strain derived, or a strain which can be derived, from a strain of the invention (or the mother strain) by means of e.g. genetic engineering, radiation and/or chemical treatment. It is preferred that the mutant is a functionally equivalent mutant, e.g. a mutant that has substantially the same, or improved, properties (e.g. regarding texture, shear stress, viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain. In the present context, the term "variant" should be understood as a strain which is functionally equivalent to a strain of the invention, e.g. having substantially the same, or improved, properties e.g. regarding texture, shear stress, viscosity, gel stiffness, mouth coating, flavor, post acidification, acidification speed, and/or phage robustness). Such variants, which may be identified using appropriate screening techniques, are a part of the present invention.

In the present context, "texture" is measured as shear stress after 12 hours growth at 37 degrees C. The SI unit for shear stress and gel stiffness is pascal (Pa).

An assay to be used for analysis of texture:

The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system. The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

LEGENDS TO THE DRAWING

EXPERIMENTAL

Example 1

Development of Phage Resistant *Streptococcus thermophilus* Strains with Improved Texture Properties Development of CHCC11977

The mother strain CHCC11342 was obtained as described in example 5. The strain is a mutant of CHCC6008 and considered to be a galactose fermenting *S. thermophilus* strain.

The strain CHCC11977 was isolated on M17 agar plate after plating 0.1 ml of an M17 over night culture of CHCC11342 together with 0.1 ml of phage CHPC1152 containing 10E09 (10exp9) phage particles per ml and incubation for two days at 37° C. One mutant, called CHCC11977, was three times colony purified and retested in plaque test on M17 agar plates at 37° C. using phage CHPC1152 where phage resistance was confirmed (no single plaques observed).

The mutant strain was then also tested in M17 broth at 37° C. in the presence of phage CHPC1152. CHCC11977 remained its phage resistance also in liquid culture, whereas CHCC11342, as expected, was attacked by CHPC1152.

CHCC11977 was also tested in milk at different temperatures (without the addition of infecting phage) showing an acidification activity comparable to the mother strain CHCC11342.

Analysis of CHCC11342 Texture in Fermented Milk

The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system.

The viscometry test was made with shear rates varying from 0.27 to 300 1/s in 21 steps. Shear rates were increased and then decreased and the upward and downward curves of shear stress and apparent viscosity were recorded.

Delay and integration times were 5 s and 10 s, respectively. For further analysis, shear stress at 300 s−1 was chosen.

Figure 1:
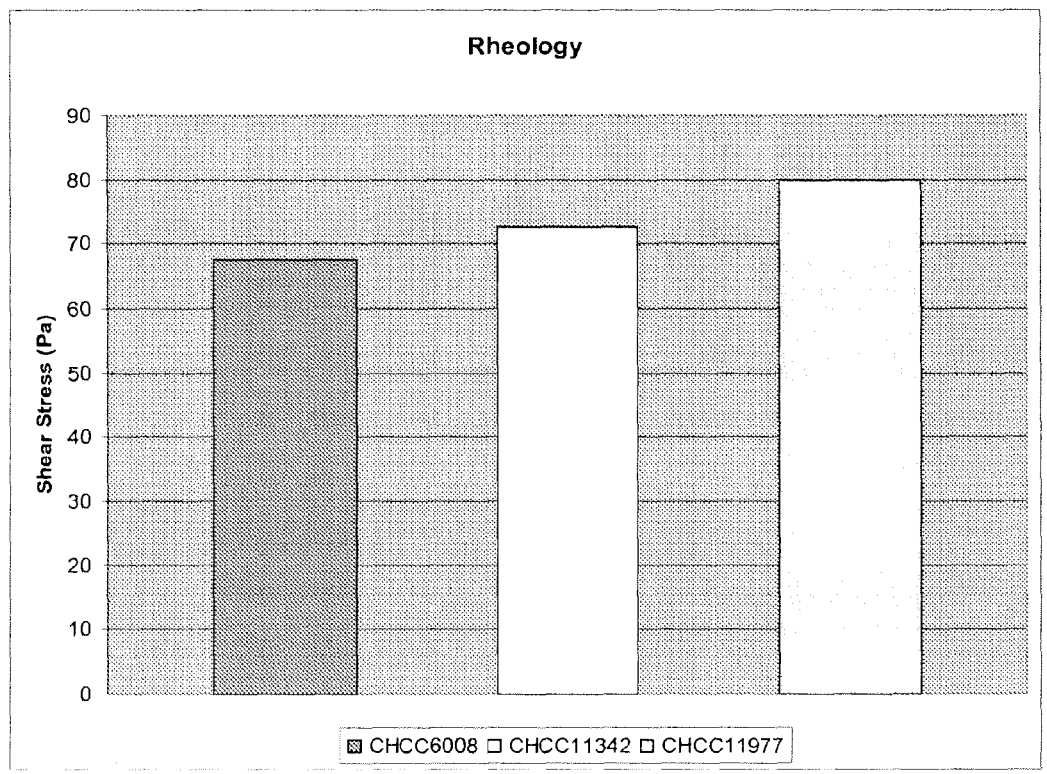
FIG. 1 depicts the shear stress of the galactose positive strain CHCC11342 and the galactose positive phage resistant mutant CHCC11977 measured with the StressTech rheometer. Shear stress was measured in coagulated milk after over/night growth in milk at 37° C.

The rheometer results showed that CHCC11342 had a shear stress value of 73.0 Pa compared to CHCC6008 with a shear stress value of 68.0 Pa, see FIG. 1.

Analysis of CHCC11977 Texture in Fermented Milk

Fermented milk was obtained, and the texture related properties were analyzed, as described above for the gal-positive phage resistant mutant.

The rheometer results showed that CHCC11977 had a shear stress value which was furthermore improved by 10% compared to CHCC11342 (shear stress value 80.0 Pa for CHCC11977 compared with 73.0 Pa for mother strain CHCC11342, see FIG. 1). Furthermore, the gel stiffness (G*) was increased by 20% for the phage resistant mutant CHCC11977 which showed a value of 126.0 Pa compared to CHCC11342 (gel stiffness 104.0 Pa). With this it was possible to improve the important rheology parameters shear stress and gel stiffness significantly by isolating a phage resistant mutant from a galactose positive mother strain.

Sequencing of the galK Promoter Region from CHCC11342

To reveal the type of mutation for the galactose positive mutant CHCC11342 the beginning of the galK gene (coding for the galactokinase from *S. thermophilus*) was sequenced.

For CHCC11342 a mutation in the region of the galK promoter was identified (see sequences below). The mutation occurred three nucleotides downstream of the −10-promoter box of the galK gene leading to a C to A nucleotide shift.

```
                                                                           SEQ ID No: 1
CHCC114342   AAAATATTGATTTTCCATGTGAAAGGGGTTACGATTTAAGTATAAACAAAAAGAATAAGTGAGATACATC

SEQ ID No: 2
CHCC6008     AAAATATTGATTTTCCATGTGAAAGGGGTTACGATTTCAGTATAAACAAAAAGAATAAGTGAGATACATC

SEQ ID No: 3
AY704368     AAAATATTGATTTTCCATGTGAAAGGGGTTACGATTTCAGTATAAACAAAAAGAATAAGTGAGATACATC

SEQ ID No: 4
Consensus    AAAATATTGATTTTCCATGTGAAAGGGGTTACGATTTCAGTATAAACAAAAAGAATAAGTGAGATACATC
                  -35                    -10                              RBS
```

Promoter region of the galK gene from CHCC11342. The point mutation within the CHCC11342 galk promoter region is indicated with grey color code. The published galK sequence from *S. thermophilus* ST111 (Genbank accession no. AY704368) is indicated for comparison. −35: −35-promoter box; −10: −10-promoter box; RBS: ribosome binding site.

Further Phage Resistant Mutants

To reveal a possible relationship between phage resistance and galactose positive phenotype five additional phage resistant mutants were isolated on M17 galactose agar plates from strain CHCC6008 (gal−) which is the mother strain of CHCC11342 (gal+). All five phage resistant mutants, CHCC11396, CHCC11397, CHCC11398, CHCC11399, and CHCC11340 (resistant to phage CHPC1152) were unable to ferment galactose meaning the gal+ phenotype is not directly related with phage resistance. On the other hand it was demonstrated by plaque assay that CHCC11342 (gal+) was still sensitive to phage CHPC1152.

Example 2

Development of Phage Resistant *Lactobacillus delbrueckii* Subsp. *Bulgaricus* Strains with Improved Texture Properties From the mother strain CHCC10019 (DSM19252), phage resistant mutants were isolated as follows:

Mutants were picked from MRS agar plates containing 10 mM $CaCl_2$/10 mM $MgCl_2$ after plating 0.1 ml of an MRS over night culture of CHCC10019 together with 0.1 ml of a CHPC658 phage lysate containing 10E06 phage particles per ml and anaerobic incubation for two days at 37° C. Thirty mutants were isolated and tested in cross-streaking towards phage CHPC658. Twenty-nine mutants appeared resistant in the cross-streaking test, and were afterwards three times colony-purified on MRS agar plates at 37° C.

The 29 mutants were tested in microtiter plates for acidification profile and phage resistance. Two microtiter plates were prepared with milk and each plate was inoculated with 2% of the respective mutant. For one plate, 2% peptone-salt diluent (control) was added to each well, and to the other microtiter plate 2% CHPC658 containing 10E06 phage particles per ml was added. The two plates were incubated at 37° C. for two days, and pH of each well was recorded every 12 minutes. All mutants were phage resistant compared to the mother strain CHCC10019, which was attacked by phage CHPC658.

Twelve mutants were chosen based on the acidification profile in MRS and milk (similar to the mother strain) and the viscosity of the strains.

Analysis of CHCC10019 Phage Resistant Mutants for Texture Properties in Fermented Milk After incubating the twelve mutants and mother strain CHCC10019 over night in milk at 37° C., the fermented milk was adjusted to 13° C. and stirred gently by means of a stick fitted with a disc containing holes until homogeneity of each sample. The rheological properties of each sample was assessed on a rheometer (StressTech, Reologica Instruments, Sweden) equipped with a C25 coaxial measuring system.

The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively. For further analysis, shear stress at 300 s−1 was chosen.

Figure 2:
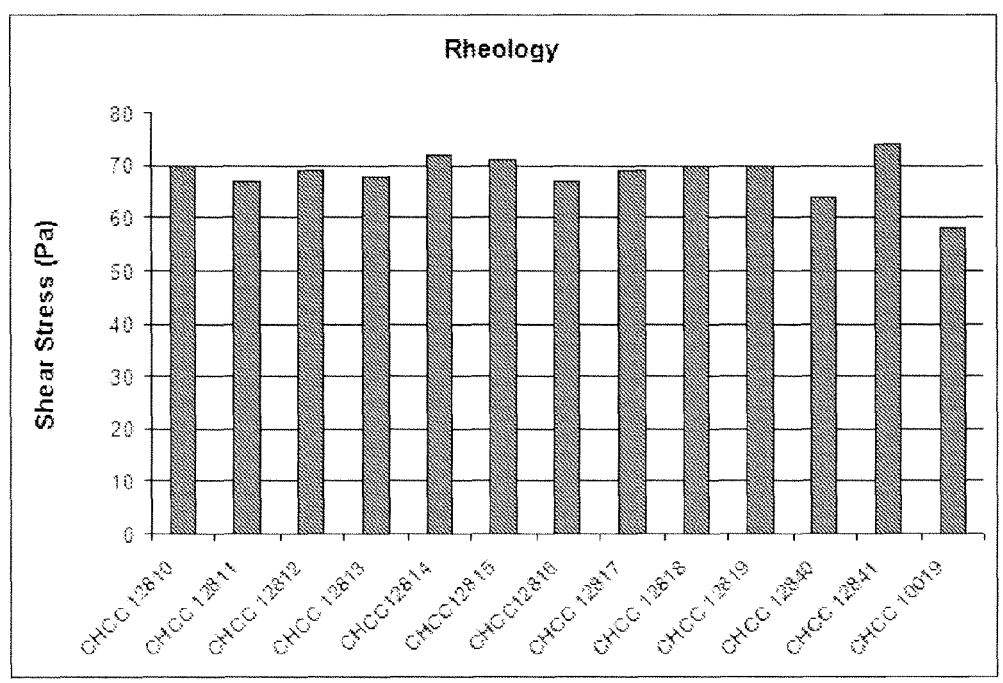
FIG. 2 depicts the shear stress of phage resistant mutants of CHCC10019 measured with StressTech rheometer. The shear stress was measured in coagulated milk after over/night growth in milk at 37° C.

The results from the rheology measurements showed that all twelve mutants (such as CHCC12813 and CHCC12841) had an improved viscosity, measured as shear stress, compared to CHCC10019. The highest shear stress value was obtained for CHCC12841 (74.0 Pa) whereas CHCC10019 had a shear stress value of 58.0 Pa, see FIG. 2. On the figure, the rheology data for the twelve phage resistant mutants is shown. All mutants have an increase in shear stress ranging from 10% up to 28% compared to CHCC10019.

Based on acidification activity and rheology data when the mutants were grown in co-culture with other strains CHCC12813 was selected as most promising candidate of the isolated mutants for further application tests.

This experiment demonstrates that the important rheological parameter shear stress of a bacterial strain will be significantly improved by isolating phage resistant mutants of the strain.

Example 3

Isolation of Phage Resistant Mutants of *Streptococcus thermophilus* Strain CHCC9204

From the mother strain CHCC9204, registered in Chr. Hansen culture collection, a phage resistant mutant was isolated. The mutant was isolated on M17-2% lactose agar plates with 10 mM $MgCl_2/CaCl_2$ after plating 0.1 ml of an M17 lactose over night culture of CHCC9204 together with 0.1 ml of phage CHPC1057 containing 1×10exp09 phage particles per ml and incubation overnight at 37° C.

Among several mutants one strain, called CHCC12339, was three times colony purified and retested in plaque test on M17 lactose agar plates at 37° C. using phage CHPC1057 for phage challenge, and phage resistance was confirmed (no single plaques observed in plaque test). CHCC12339 was also tested in milk showing an acidification activity comparable to the mother strain.

Analysis of Texture Properties of Phage Resistant Mutant CHCC12339 in Fermented Milk After mutant CHCC12339 and mother strain CHCC9204 were incubated over night in milk at 37° C., the fermented milk was brought to 13° C. and stirred gently by means of a stick fitted with a bored disc until homogeneity of each sample. The rheological properties of each sample was assessed on a rheometer (StressTech, Reologica Instruments, Sweden) equipped with a C25 coaxial measuring system.

The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively. For further analysis, shear stress at 300 s−1 was chosen.

Figure 3:
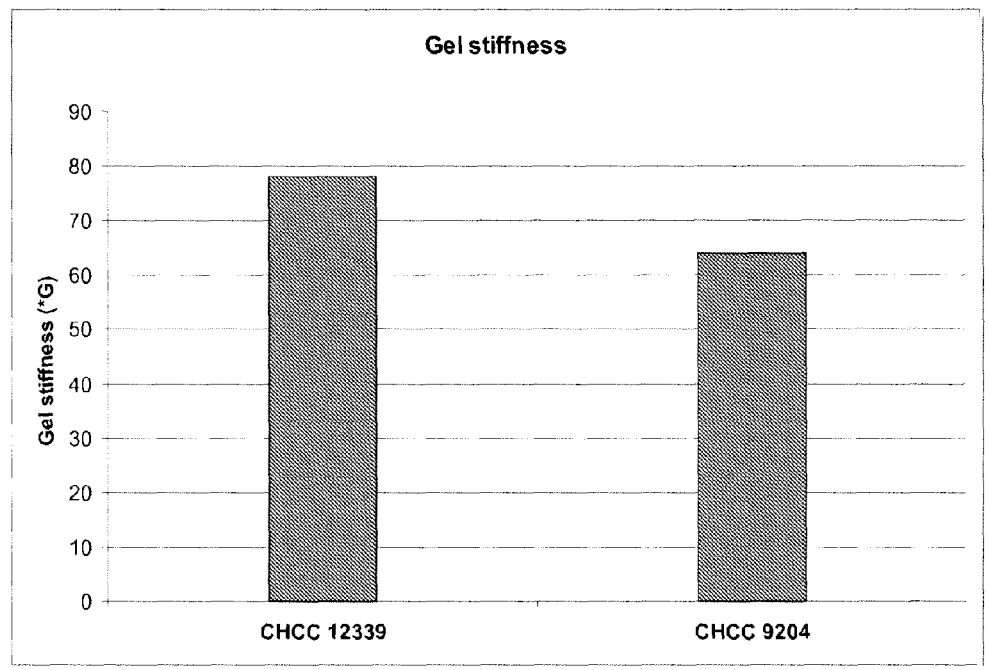
FIG. 3 depicts the gel stiffness of CHCC12339, phage resistant mutant of CHCC9204, measured with StressTech rheometer. The gel stiffness was measured in coagulated milk after over/night growth in milk at 37° C.

The results from the rheology measurements showed that mutant CHCC12339 leads to an increase of gel stiffness (G*) by 22% compared to CHCC9204, see FIG. 3. On the figure, the gel stiffness values (G*) for the phage resistant mutant CHCC12339 (78.0 Pa) and mother strain CHCC9204 (64.0 Pa) are compared.

Example 4

Isolation of Phage Resistant Mutants of *Streptococcus thermophilus* Strain CHCC5086

From the mother strain CHCC5086, registered in Chr. Hansen culture collection, a phage resistant mutant was isolated.

The mutant was isolated on M17-2% lactose agar plates with 10 mM $MgCl_2/CaCl_2$ after plating 0.1 ml of an M17-2% lactose over night culture of CHCC5086 together with 0.1 ml of phage CHPC1089 containing 1×10exp08 phage particles per ml and incubation overnight at 37° C. Among several mutants one strain, called CHCC13140, was three times colony purified and retested in plaque on M17 lactose agar plates at 37° C. test using phage CHPC1089 for phage challenge, and phage resistance was confirmed (no single plaques observed in plaque test). CHCC13140 was also tested in milk acidification test showing an acidification activity comparable to the mother strain.

Analysis of Texture Properties of Phage Resistant Mutant CHCC13140 in Fermented Milk After mutant CHCC13140 and mother strain CHCC5086 were incubated over night in milk at 37° C., the fermented milk was brought to 13° C. and stirred gently by means of a stick fitted with a bored disc until homogeneity of each sample. The rheological properties of each sample was assessed on a rheometer (StressTech, Reologica Instruments, Sweden) equipped with a C25 coaxial measuring system.

The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively. For further analysis, shear stress at 300 s−1 was chosen.

Figure 4:
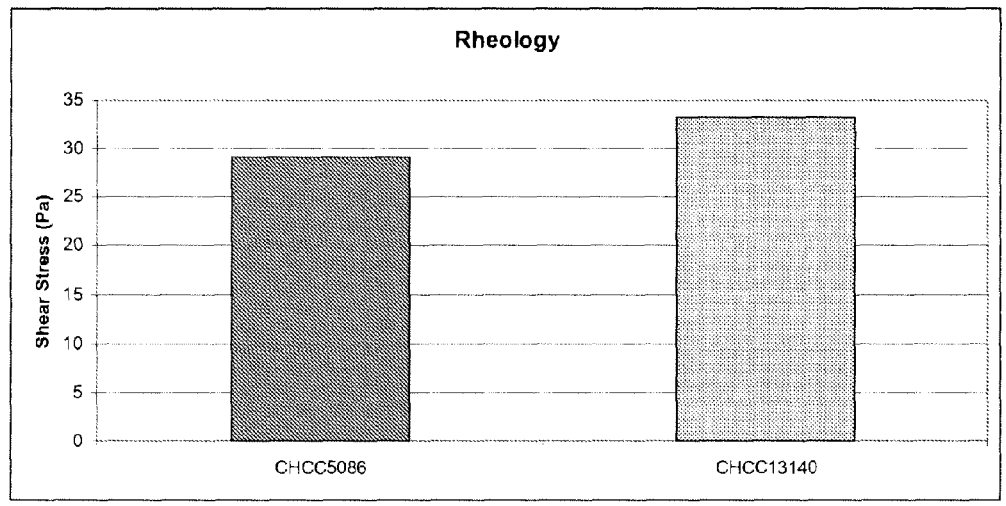
FIG. 4 depicts the shear stress of CHCC13140, phage resistant mutant of CHCC5086, measured with StressTech rheometer. The shear stress was measured in coagulated milk after over/night growth in milk at 37° C.

The results from the rheology measurements showed that mutant CHCC13140 leads to an increase of shear stress by 14% compared to CHCC5086, see FIG. 4. On the figure, the shear stress data for the phage resistant mutant CHCC13140 (shear stress 33.0 Pa) and mother strain CHCC5086 (28.0 Pa) are compared.

Example 5

Preparation of a Galactose Positive Mutant of a *Streptococcus* Strain

General Method for Obtaining Gal+ Strains

Prior to the mutant isolation the mother strain (e.g. CHCC6008) were streaked on M17 agar plates with 2% galactose (M17-gal plates). CHCC6008 did not grow on galactose as sole carbohydrate source, and thus the mother stain is considered to be gal−.

Over night cultures of the mother strain were then plated on M17-gal plates and several colonies could be isolated after two days of growth at 37° C.

Several mutants were purified on M17-gal plates and retested in M17 broth containing 2% galactose as sole carbohydrate.

A mutant may be obtained by means of e.g. genetic engineering, radiation and/or chemical treatment, or the mutant may be a spontaneous mutant.

A mutant was considered galactose positive when the pH was reduced by a value of at least 1.0 after 16 hours incubation at 37 degrees C. in M17 with 2% galactose (galactose added as sole carbohydrate), inoculated in an amount of at least 10E4 cells pr ml of medium.

Whereas CHCC6008 did not lower the pH in M17-gal broth significantly, CHCC11342, one of the purified mutants, reached a pH of 5.4 after 16 hours at 37° C., and was therefore considered a galactose-fermenting (gal+) mutant of CHCC6008.

Isolation of Galactose Fermenting Strains

Mutants were isolated as galactose fermenting mutant of *S. thermophilus* strain CHCC6008 (=ST6008, DSM18111). The CHCC6008 cells were neither mutagenized with any mutagenic compound nor by UV light prior to the mutant isolation step. The isolated strains resemble therefore spontaneous galactose positive mutants of CHCC6008.

Prior to the mutant isolation CHCC6008 was streaked on M17 agar plates with 2% galactose (M17-gal plates). CHCC6008 did not grow on galactose as sole carbohydrate source.

Over night culture of CHCC6008 were then plated on M17-gal plates and several colonies could be isolated after two days of growth at 37° C. Several mutants were purified on M17-gal plates and retested in M17 broth containing 2% galactose as sole carbohydrate.

Whereas CHCC6008 did not lower the pH in M17-gal broth significantly, CHCC11379, one of the purified mutants, reached a pH of 5.3 after 10 hours at 37° C., and was therefore considered a galactose-fermenting mutant from CHCC6008.

Strains CHCC11342 and CHCC11976 were isolated the same way.

Isolation of Mutants by Genetic Engineering

Galactose positive mutants can also be generated by site directed mutagenesis. Oligonucleotides carrying the mutated nucleotide within the galK −10 promoter box is used to amplify a specific DNA fragment by PCR. The PCR fragment carrying the desired mutation is cloned into a vector plasmid and transformed into the *S. thermophilus* target strain, and the mutation is integrated into the chromosome and exchanging the wild type galK promoter region by recombination. Isolation of strains is done as above.

Analysis of Texture in Fermented Milk

The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system.

The viscometry test was made with shear rates varying from 0.27 to 300 1/s in 21 steps.

Shear rates were increased and then decreased and the upward and downward curves of shear stress and apparent viscosity were recorded.

Delay and integration times were 5 s and 10 s, respectively. For further analysis, shear stress at 300 s−1 was chosen. The rheometer results showed that CHCC11379 had a shear stress which was improved by 10% compared to CHCC6008 (shear stress value 74.0 Pa (Pascals) for CHCC11379 compared with 67.5 Pa for mother strain CHCC6008.

Analysis of Texture in Milk

In another experiment CHCC11379 was used as a part of a yoghurt culture where strains from *S. thermophilus* are co-cultured in skimmed milk at 43° C. together with a strain from the species *Lactobacillus delbrueckii* ssp. *bulgaricus*. When the only difference in the production of yoghurt was the use of CHCC11379 instead of wild type CHCC6008 the shear stress was also increased by 10% (105.0 Pa for the yoghurt culture containing CHCC11379 compared with 94.7 Pa for the yoghurt culture containing CHCC6008).

Sequencing of the galK Promoter Region from CHCC11379

To reveal the type of mutation for the gal positive mutant CHCC11379 the beginning of the galK gene (coding for the galactokinase from *S. thermophilus*) was sequenced.

For CHCC11379 a mutation in the region of the galK promoter was identified (see below). The respective mutation will most likely lead to a stronger promoter activity compared to the mother strain 6008, explaining the observed gal-positive phenotype. This is based on the fact that the consensus sequence for the −10-promoter box is "TATAAT", and that a mutation at nucleotide 3 of the −10 box (region) for CHCC6008 ("TACGAT") leads to a −10 box with a higher similarity to the consensus sequence in CHCC11379 ("TAT-GAT").

AY704368) is indicated for comparison. −35: −35-promoter region; −10: −10-promoter region; RBS: ribosome binding site.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

DEPOSITS AND EXPERT SOLUTION

The strains *Streptococcus thermophilus* CHCC11977 and CHCC11342 were deposited at DSMZ (Deutsche Sammlung von Mikroorganismen and Zellkulturen GmbH, Inhoffenstr. 7B, D-38124 Braunschweig, Germany) under the accession numbers DSM22935 and DSM22932, resp., on Sep. 8, 2009. CHCC6008 has been deposited at DSMZ under the accession number DSM 18111 on Mar. 29, 2006.

Bacteriophages CHPC658, CHPC1057 and CHPC1152 were deposited at DSMZ on 27 Aug. 2010, and given the deposit numbers DSM23961, DSM23962, and DSM23994, resp.

Further deposits at DSMZ:
CHCC10019 (DSM19252) and CHCC3984 (DSM19251): Date of deposit 3 Apr. 2007,
CHCC2008 (DSM22584) and CHCC5086 (DSM22587): date of deposit 19 may 2009,
CHCC11379 (DSM22884): date of deposit 26 Aug. 2009,
CHCC11976 (DSM22934): date of deposit 8 Sep. 2009;
CHCC13140 (DSM 24023), CHCC12813 (DSM24074), and CHPC1089 (DSM 24022): date of deposit 29 Sep. 2010;
CHCC12339 (DSM24090): date of deposit 14 Oct. 2010.
*Streptococcus thermophilus* CHCC5086 (DSM22587): date of deposit: 19 May 2009.
CHCC9204 (DSM19243): date of deposit 29 Mar. 2007.

```
                                                                    SEQ ID No: 5
CHCC11379  AAAATATTGATTTTCCATGTGAAAGGGGTTATGATTTCAGTATAAACAAAAAGAATAAGTGAGATACATC

SEQ ID No: 2
CHCC6008   AAAATATTGATTTTCCATGTGAAAGGGGTTACGATTTCAGTATAAACAAAAAGAATAAGTGAGATACATC

SEQ ID No: 3
AY704368   AAAATATTGATTTTCCATGTGAAAGGGGTTACGATTTCAGTATAAACAAAAAGAATAAGTGAGATACATC

SEQ ID No: 4
Consensus  AAAATATTGATTTTCCATGTGAAAGGGGTTACGATTTCAGTATAAACAAAAAGAATAAGTGAGATACATC
              -35                        -10                        RBS
```

Promoter region of the galK gene from CHCC11379. The point mutation within the CHCC11379 galk promoter is indicated with grey color code. The published galK sequence from *S. thermophilus* ST111 (Genbank accession no.

The deposits have been made under the conditions of the Budapest Treaty on the International Recognition of the Deposit of Microorganisms for the Purposes of Patent Procedure.

REFERENCES

Appl. Environ. Microbiol. 71, 7, p. 3659-67 (2005);
International Journal of Food Microbiology 113 (2007) 195-200;
Applied And Environmental Microbiology, February 2002, p. 784-790;
J Dairy Sci 92: 477-482 (2009)
WO2008/040734A1, WO2007/025097A2, U.S. Pat. No. 7,241,610B2, WO2007/144770A2, WO2004/085607A, WO2008/148561A, WO11000879A, WO11000883A, WO10023178A All references cited in this patent document are hereby incorporated herein in their entirety by reference.

The invention claimed is:

1. A lactic acid bacterium having a mutation in the region between the Pribnow box and the ribosome binding site of the galactokinase (galK) gene, wherein the mutation results in the replacement of C in the sequence TTCAGT (SEQ ID NO:6) downstream from the wildtype Pribnow box with a nucleotide selected from the group consisting of A and G.

2. The lactic acid bacterium according to claim 1, which belongs to a species selected from the group consisting of *Streptococcus thermophilus* and *Lactobacillus delbrueckii* subsp. *bulgaricus*.

3. The lactic acid bacterium according to claim 1, which generates a shear stress in fermented milk from 60 to 100 Pa, measured after 12 hours of growth at 37° C., when inoculated in an amount of at least 10E4 cells/mL milk.

4. The lactic acid bacterium according to claim 1, belonging to a bacterial strain of the species *Streptococcus thermophilus* selected from the group consisting of CHCC11342 (DSM 22932), CHCC11976 (DSM 22934), and mutants or variants derived from any of these deposited strains having all the identifying characteristics of the deposited strain.

5. The lactic acid bacterium according to claim 4, wherein the lactic acid bacterium is a mutant or variant derived from one of said deposited strains that generates an increased shear stress in fermented milk compared to the mother strain of said deposited strain, measured after 12 hours of growth at 37° C., when inoculated in an amount of at least 10E4 cells/mL milk.

6. The lactic acid bacterium according to claim 5, wherein the shear stress in fermented milk is increased by at least about 10% compared to that of the mother strain of said deposited strain.

7. The lactic acid bacterium according to claim 1, wherein the galK gene further comprises a −10 region having a nucleotide sequence selected from the group consisting of TATGAT (SEQ ID NO:8), TATTAT (SEQ ID NO:9) and TACTAT (SEQ ID NO:10).

8. A composition comprising the lactic acid bacterium of claim 1.

9. A method for producing a fermented milk product, comprising fermenting a milk substrate with a lactic acid bacterium of claim 1.

* * * * *

SEQUENCE LISTING

```
<160> NUMBER OF SEQ ID NOS: 10

<210> SEQ ID NO 1
<211> LENGTH: 70
<212> TYPE: DNA
<213> ORGANISM: Streptococcus thermophilus

<400> SEQUENCE: 1
aaaatattga ttttccatgt gaaaggggtt acgatttaag tataaacaaa aagaataagt      60
gagatacatc                                                             70

<210> SEQ ID NO 2
<211> LENGTH: 70
<212> TYPE: DNA
<213> ORGANISM: Streptococcus thermophilus

<400> SEQUENCE: 2
aaaatattga ttttccatgt gaaaggggtt acgatttcag tataaacaaa aagaataagt      60
gagatacatc                                                             70

<210> SEQ ID NO 3
<211> LENGTH: 70
<212> TYPE: DNA
<213> ORGANISM: Streptococcus thermophilus

<400> SEQUENCE: 3
aaaatattga ttttccatgt gaaaggggtt acgatttcag tataaacaaa aagaataagt      60
gagatacatc                                                             70

<210> SEQ ID NO 4
<211> LENGTH: 70
<212> TYPE: DNA
<213> ORGANISM: Streptococcus thermophilus

<400> SEQUENCE: 4
aaaatattga ttttccatgt gaaaggggtt acgatttcag tataaacaaa aagaataagt      60
gagatacatc                                                             70

<210> SEQ ID NO 5
<211> LENGTH: 70
<212> TYPE: DNA
<213> ORGANISM: Streptococcus thermophilus

<400> SEQUENCE: 5
aaaatattga ttttccatgt gaaaggggtt atgatttcag tataaacaaa aagaataagt      60
gagatacatc                                                             70

<210> SEQ ID NO 6
<211> LENGTH: 6
<212> TYPE: DNA
<213> ORGANISM: Streptococcus thermophilus
```

```
<400> SEQUENCE: 6 ttcagt                                                                         6

<210> SEQ ID NO 7
<211> LENGTH: 6
<212> TYPE: DNA
<213> ORGANISM: Streptococcus thermophilus

<400> SEQUENCE: 7 tacgat                                                                         6

<210> SEQ ID NO 8
<211> LENGTH: 6
<212> TYPE: DNA
<213> ORGANISM: Streptococcus thermophilus

<400> SEQUENCE: 8 tatgat                                                                         6

<210> SEQ ID NO 9
<211> LENGTH: 6
<212> TYPE: DNA
<213> ORGANISM: Streptococcus thermophilus

<400> SEQUENCE: 9 tattat                                                                         6

<210> SEQ ID NO 10
<211> LENGTH: 6
<212> TYPE: DNA
<213> ORGANISM: Streptococcus thermophilus

<400> SEQUENCE: 10 tactat                                                                         6
```